United States Patent [19]

Dobritz

[11] 4,048,993
[45] Sept. 20, 1977

[54] HUMIDITY EXCHANGER IN AN APPARATUS FOR RESPIRATION AND ANASTHESIA

[75] Inventor: Gunter Dobritz, Lubeck, Germany

[73] Assignee: Dragerwerk Aktiengesellschaft, Germany

[21] Appl. No.: 690,840

[22] Filed: May 28, 1976

[30] Foreign Application Priority Data

June 30, 1975 Germany .............................. 2529050

[51] Int. Cl.² ........................................... A61M 16/00
[52] U.S. Cl. .................................. 128/212; 128/192; 55/269; 261/104; 261/DIG. 65
[58] Field of Search ............... 128/212, 185, 186, 187, 128/188, 191 R, 192, 195, 204, 205, 146, 147; 55/269; 261/104

[56] References Cited

U.S. PATENT DOCUMENTS

| 2,610,038 | 9/1952 | Phillips | 128/146 |
| 3,976,450 | 8/1976 | Marcote et al. | 55/269 |

FOREIGN PATENT DOCUMENTS

| 85,055 | 2/1958 | Denmark | 128/212 |
| 2,223,474 | 11/1973 | Germany | 128/212 |

*Primary Examiner*—Kyle L. Howell
*Assistant Examiner*—Henry J. Recla

*Attorney, Agent, or Firm*—McGlew and Tuttle

[57] ABSTRACT

A humidity exchanger in an apparatus for respiration and anasthesia comprises an inhalation air conduit which is juxtaposed to an exhalation air conduit and separated therefrom by a diffusion foil which permits the passage of a vapor therethrough but not a liquid. Both the inhalation and exhalation conduits are connected at their one ends to the respirator and at their opposite ends they are connected together and to a mouthpiece for use by the patient. The temperatures in both conduits adjacent the mouthpiece are maintained at temperatures so that there is a temperature difference between the inhalation air and the exhalation air in the respective conduits to thus provide a condensation zone. Another zone is provided toward the opposite end of the two conduits in which the temperatures between the air and the two conduits is maintained substantially the same so as to define a diffusion zone. The foil advantageously comprises a fluorinated hydrocarbon polymer which is hygroscopic. The entire humidity exchanger comprising the two conduits is advantageously surrounded by heat insulation and the exhaling duct may advantageously be provided with a heater adjacent the mouthpiece end in the condensation zone. The inhalation air conduit is also advantageously provided with a humidifier.

7 Claims, 2 Drawing Figures

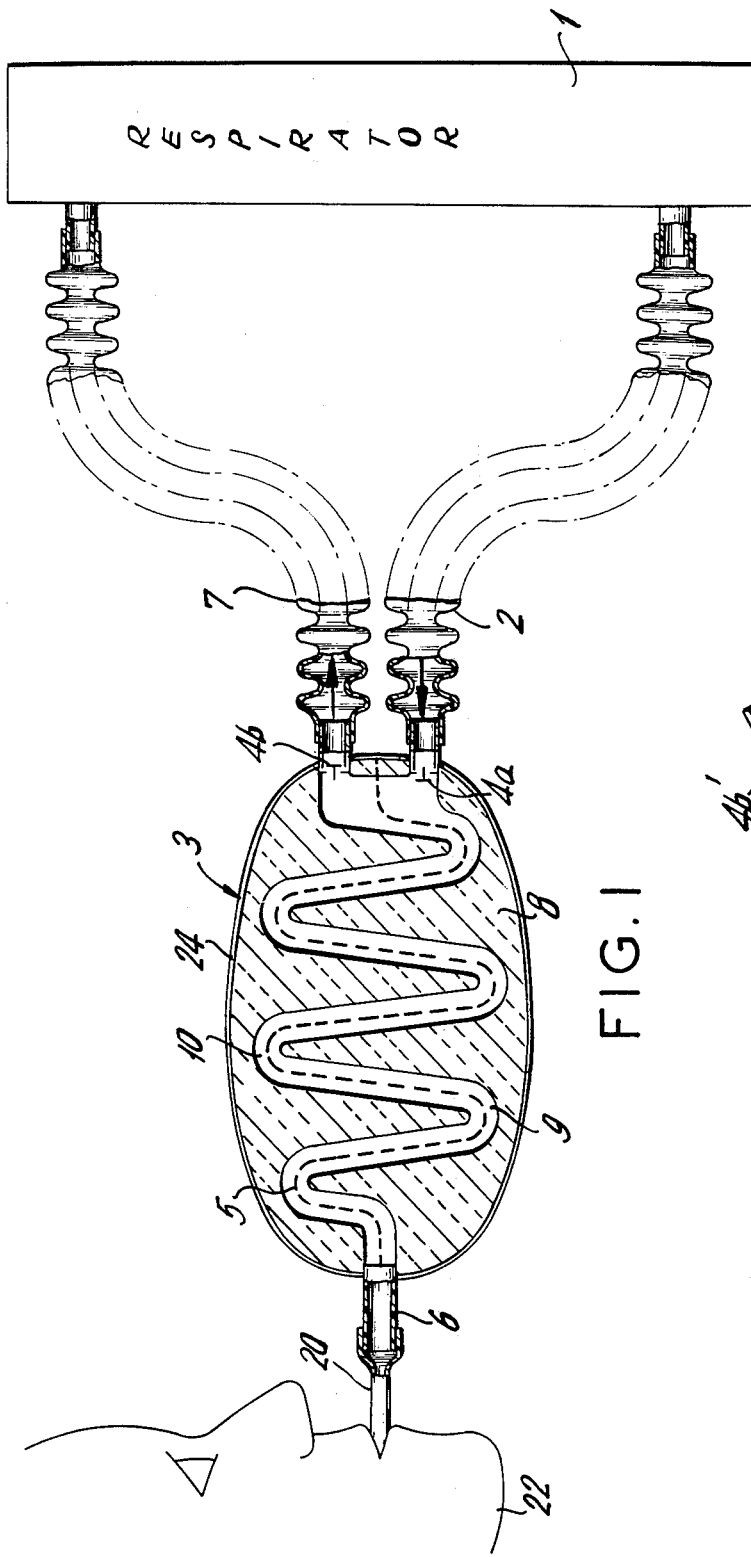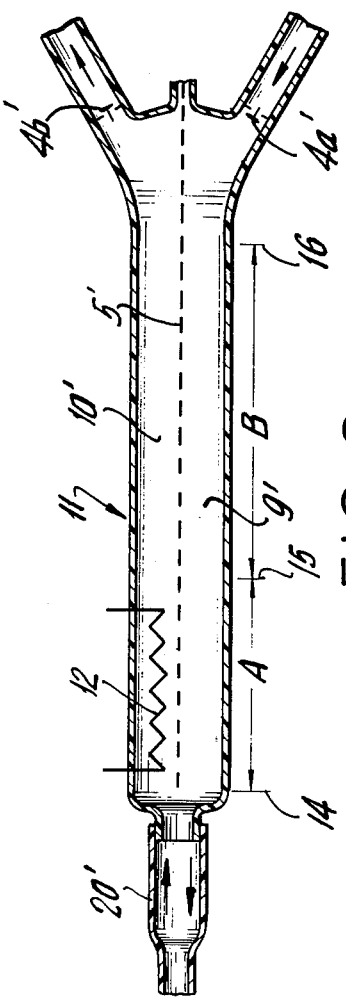

HUMIDITY EXCHANGER IN AN APPARATUS FOR RESPIRATION AND ANASTHESIA

BACKGROUND OF THE INVENTION

1. Field of the Invention

This invention relates in general to the construction of breathing apparatus and in particular to a new and useful humidity exchanger in an apparatus for respiration and anasthesia wherein the humidity contained in the exhaling air is separated therefrom and the separated water is evaporated into the inhaling air.

2. Description of the Prior Art

In apparatus for respiration and anasthesia it must be made certain that the respiratory tracts of the patient do not dry out. The risk of the patient's tracts drying out exists particularly when the inhaling air is fed to the patient through an intratracheal catheter or through a tracheotomy canule. This is because the rinopharyngal area which normally moistens the inhaling air is then bypassed.

A known apparatus for such use comprises a heat container arranged in the heat cover and connected to the nose or mouth through a tube which is filled with metal particles such as filings or wire pieces. The tube is divided into two compartments to insure the flow of the exhaling air and the inhaling air on different paths. Valves control the air through the compartments. An asbestos lining can be saturated with water to moisten the inhaling air. The exhaling air always flows through one compartment while the inhaling air always flows through the other compartment. The exhaling air heats the heated container which is also heated by the body temperature of the head. In the heat exchanger the inhaling air takes over the heat from the heat container. In the heat container it is only slightly cooled by colder inhaling air if it is cooled at all and this is due to the additional heating by the body temperature so that there is little condensation of water from the exhaling air. In addition this condensed moisture remains in the compartment that is traversed only by the exhaling air. The bulk of the water is eliminated with the exhaling air. Moistening of the inhaling air is thus not achieved. Such moistening can only be effected by the water from the asbestos lining. Moistening therefore depends on the care of the attendant. This machine is not known for use in connection with apparatus for artificial respiration and anasthesia.

Another known humidity exchanger in which the humidity contained in the exhaling air is separated and the separated water of condensation is evaporated into the inhaing air includes a steam condenser which is filled with metal wires, screens or cloths, etc. It can also be filled with a porous material of good thermal conductivity. The connection between the parts of the steam condenser and the exhaling air and the inhaling line are so designed that the water can pass through. Hence only the condensed water is picked up in the inhaling air current. But since condensation takes place only until the temperature is equalized between the exhaling air and the inhaling air current, only the portion obtained from the exhaling air current can be utilized for moistening the inhaling air. A disadvantage is that the water contained in the exhaling air which still has a relative humidity of 100% after temperature equalization with the inhaling air discharged.

SUMMARY OF THE INVENTION

The present invention provides a humidity exchanger for apparatus for respiration and anasthesia with which the humidity and heat contained in the exhaling air are transferred as completely as possible into the inhaling air. In accordance with the invention the ducts carrying the inhaling and exhaling air in counterflow are arranged in juxtaposition and have a common partition in the diffusion foil. The construction provides a condensation zone located in the direction of flow of the exhaling air in which there is a temperature difference relative to the inhaling air and a diffusion zone adjacent thereto in which the inhaling and exhaling air have the same temperatures.

The advantages achieved with the construction of the invention are that due to the use of a diffusion foil, the condensed water in the condensation zone and the water contained in the adjacent diffusion zone in the exhaling air in vapor form diffuse through the diffusion foil into the inhaling air. The heat transfer is very good because of the small thickness of the foil. The specific thermal conductivity is practically irrelevant. This solution means an extraordinary reduction of the safety risk for the patient in respiration. In the respiration of a tracheotomized patient for example the necessary humidity and heat in the inhaling air is insured by the full and reliable utilization of the humidity and heat from the exhaling air.

In accordance with a feature of the invention the material of the diffusion foil comprises a fluorinated hydrocarbon polymer. The good diffusion properties of this material relative to water and steam are known. The foil permits the passing of the humidity both in a condensation zone and in the diffusion zone without difficulty. Due to this hygroscopic property of the diffusion foil it is possible to improve the diffusion properties at low temperatures.

In a further development the humidity exchanger is advantageously surrounded by heat insulation. This insures in a simple manner that the heat contained in the exhaling air can not escape through the outer surface into the surrounding atmosphere. Such an insulation does not require great technical effort and can be safely controlled in the actual construction of such a device.

For special uses such as when there is a cold atmosphere the exhaling duct in the condensation zone advantageously includes a heater. By heating the exhaling air the condensation zone is extended and the ratio to the diffusion zone thus changed. Due to the longer condensation zone more water is fed to the inhaling air which is always dry at such location because of its relatively low temperature. In addition the temperature of the inhaling air is increased. Such conditions are extremely advantageous when there are extremely low outside temperatures.

Another special design is obtained with a humidifier arranged ahead of the inhaling air duct. With this additional device it is possible to use an extremely dry and hot inhaling air for respiration.

Accordingly it is an object of the invention to provide a humidity exchanger in an apparatus for respiration and anasthesia in which the humidity contained in the exhaling air is separated and the separated water is evaporated into the inhaling air and which includes juxtaposed inhalation and exhalation ducts arranged in counterflow arrangement relative to each other and having a partition therebetween in the form of a diffusion foil and wherein the two ducts contain in series in the direction of flow of the exhaling air a condensation zone in which there is a temperature difference relative to the inhaling air and directly adjacent thereto a diffusion zone in which the same temperatures of the inhaling and exhaling air exist.

A further object of the invention is to provide an apparatus in which inhalation and exhalation conduits are arranged in juxtaposition with a diffusion foil therebetween in which an interconnected end adapted to be connected to a mouthpiece for a patient at an opposite end with connections for a respirator and which is surrounded by insulation so as to maintain a condensation zone adjacent the mouthpiece end of the conduits and a diffusion zone alongside the condensation zone extending toward the connections to the respirator and wherein the conduits are advantageously surrounded by insulation and for extremely cold weather use the exhalation duct in the condensation zone advantageously includes a heater and the inhalation duct is advantageously connected to a moisturizer.

A further object of the invention is to provide an apparatus for use with respiration and anasthetic devices which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawings and descriptive matter in which there are illustrated preferred embodiments of the invention.

BRIEF DESCRIPTION OF THE DRAWINGS

In the drawings:

FIG. 1 is a schematic sectional view of a humidity exchanger for use with either respiration or anesthesia and constructed in accordance with the invention; and FIG. 2 is a view similar to FIG. 1 of a somewhat modified embodiment and indicating the various condensation and diffusion zones.

GENERAL DESCRIPTION OF THE PREFERRED EMBODIMENTS

Referring to the drawings in particular the invention embodied therein in FIG. 1 comprises a humidity exchanger generally designated 3 which is used with a respirator 1. The humidity exchanger 3 includes juxtaposed inhalation air duct or conduit portion 9 and an exhalation air duct or conduit portion 10 which are separated by a partition wall which comprises a diffusion foil 5. The one ends of the two conduit portions are interconnected by a line 6 and provided with a mouthpiece connection 20 which is adapted to be positioned in the mouth of a patient 22. The opposite ends of the two conduits 9 and 10 are connected respectively to the exhaling air conduit 7 and the inhaling air conduit 2. Check valves 4a and 4b are located in the respective conduits to permit the flow of the air in the direction of the arrows as indicated.

In accordance with the invention the diffusion foil 5 separates the warm and humid exhaling air in the conduit portion 10 from the cold and dry inhaling air in the conduit portion 9. The heat and humidity are equalized in counterflow heat transfer over the diffusion foil 5. The material of the diffusion foil 5 is a material from the series of fluorinated hydrocarbon polymers having hygroscopic properties. The inhaling air is thus brought to the temperature and humidity of the exhaling air by diffusion and heat transfer from the exhaling air. In order to avoid heat losses, the humidity exchanger has temperature control means in the form of a heat insulation 8 in a casing 24 which surrounds the two conduit portions.

FIG. 2 shows a simplified embodiment of a humidity exchanger generally designated 11. In essence it differs from the humidity exchanger of the first embodiment in that the temperature control means comprises an electric heater 12 disposed in the exhaling air conduit 10'. The heater 12 is located directly adjacent a connection to the mouthpiece 20' at the location of the inlet to the exhaling air duct 10'.

The operation of the humidity exchanger 3 as well as the humidity exchanger 11 is as follows:

In use for example in respiration, two zones are formed due to the operation between the boundaries 14 and 16 which are defined adjacent the extremities of the diffusion foil 5 of 5' as schematically indicated. The first condensation zone A between the boundaries 14 and 15 and the diffusion zone B between the boundaries 15 and 16 are produced by the flow of the inhalation air through the conduit 9' and the flow of the exhalation air through the conduit 10'. In the condensation zone A there is a heat gradient between the inhaling and the exhaling air. The heat gradient effects the condensation of the water from the exhaling air on diffusion foil 5. The water thus evaporates after diffusing through the diffusion foil 5 on the other side into the inhaling air conduit 9'. In this portion of the humidifier therefore the bulk of this water passes from the exhaling air into the inhaling air. In the diffusion zone B which adjoins the condensation zone A additional water enters into the inhalation stream in the conduit 9' but only in the form of a steam which passes through the diffusion foil 5 into the inhaling air which at this location is still very dry.

For special applications for example when used in low temperatures of the inhaling air, the exhaling air is heated by a heater 12 which is located in the condensation zone A and thus has the effect of extending the length of the condensation zone. An adequate passage of water from the exhalation zone to the inhaling air is thus effected.

While specific embodiments of the invention have been shown and described in detail to illustrate the application of the principles of the invention, it will be understood that the invention may be embodied otherwise without departing from such principles.

What is claimed is:

1. A humidity exchanger apparatus for respiration and anesthesia, comprising a combined breathing conduit having a partition wall extending longitudinally therethrough and comprising a diffusion foil, said conduit with said partition defining a separate inhalation passage in juxtaposed relation to a separate exhalation passage, a mouthpiece connected to said combined breathing conduit and interconnecting said passages adjacent one end, a respirator connection connected to said combined breathing conduit adjacent the opposite end and having a separate inhalation conduit connected to said inhalation passage and exhalation conduit connected to said exhalation passage and having valve means permitting inhalation air and exhalation air to pass in respective opposite directions through said inhalation and exhalation passages and conduits, and a first portion of said breathing conduit adjacent said one end of said breathing conduit defining a condensation zone, a second portion of said breathing conduit between said first portion and said opposite end defining a diffusion zone, and temperature control means to maintain said condensation zone of a predetermined length of said inhalation and exhalation conduit portions adjacent said one end at temperatures in which the air passing through said inhalation and exhalation conduit portions have a temperature difference in said condensation zone and also to maintain said diffusion zone of corresponding length of said inhalation and exhalation conduit portions adjacent said opposite end at temperatures which are substantially equal.

2. An apparatus according to claim 1, wherein said diffusion foil comprises a fluorinated hydrocarbon polymer.

3. An apparatus according to claim 1, wherein said diffusion foil is hygroscopic.

4. An apparatus according to claim 1, wherein said temperature control means includes heat insulation surrounding said breathing conduit in the condensation zone and the diffusion zone.

5. An apparatus according to claim 1, wherein said temperature control means includes a heater in said exhalation passage in said condensation zone.

6. A humidity exchanger for use with respiration and anasthesia apparatus, comprising a single breathing conduit defining an inhalation air conduit portion and an exhalation conduit portion juxtaposed to said inhalation conduit portion, a diffusion foil separating said inhalation and exhalation conduit portions, said inhalation and exhalation conduit portions having means at one end for connecting inhalation and exhalation conduits of a respirator to the respective inhalation and exhalation conduit portions and at the opposite end, means for interconnecting said inhalation and exhalation conduit portions with a patient's connection for a user of the apparatus, and means for directing inhalation and exhalation air through said respective inhalation and exhalation conduit portions in respective opposite directions, a first portion of said breathing conduit adjacent said one end of said breathing conduit defining a condensation zone, a second portion of said breathing conduit between said first portion and said opposite end defining a diffusion zone, and temperature control means to maintain said condensation zone of a predetermined length of said inhalation and exhalation conduit portions adjacent said one end at temperatures in which the air passing through said inhalation and exhalation conduit portions have a temperaure difference in said condensation zone and also to maintain said diffusion zone of corresponding length of said inhalation and exhalation conduit portions adjacent said opposite end at temperatures which are substantially equal.

7. A method of handling air to and from a respirator in a patient's mouth to condition it for proper temperature and humidity for the patient using a conduit system including a single breathing conduit defining an inhalation air conduit portion and an exhalation conduit portion juxtaposed to said inhalation conduit portion, a diffusion foil separating said inhalation and exhalation conduit portions, said inhalation and exhalation conduit portions having means at one end for connecting inhalation and exhalation conduits of the respirator to the respective inhalation and exhalation conduit portions and at the opposite end, means for interconnecting said inhalation and exhalation conduit portions with a patient's connection for a user of the apparatus, and means for directing inhalation and exhalation air through said respective inhalation and exhalation circuit portions in respective opposite directions, a first portion of said breathing conduit adjacent said one end of said breathing conduit defining a condensation zone, a second portion of said breathing conduit between said first portion and said opposite end defining a diffusion zone, and temperature control means to maintain said condensation zone of a predetermined length of said inhalation and exhalation conduit portions adjacent said one end at temperatures in which the air passing through said inhalation and exhalation conduit portions have a temperature difference in said condensation zone and also to maintain said diffuson zone of corresponding length of said inhalation and exhalation conduit portions adjacent said opposite end at temperatures which are equal, comprising directing inhalation air from said respirator through said inhalation conduit portion and thereby, alongside said porous membrane and directing the exhalation air from the patient's mouth to the respirator through the exhalation conduit portion simultaneously and controlling the temperature of said conduit portions via said temperature control means so that there is a condensation produced in said condensation zone adjacent the person's mouth wherein the inhalation air is conditioned as to temperature and moisture before it enters the person's mouth and so that there is a transfer of liquid or moisture from one conduit portion to the other in said diffusion zone.

* * * * *